(12) United States Patent
Chuang et al.

(10) Patent No.: US 9,517,998 B1
(45) Date of Patent: Dec. 13, 2016

(54) DEVICE METHOD OF MAKING, SEPARATING, AND PURIFYING ARTEPILLIN C IN PROPOLIS

(71) Applicant: Ming-Hsi Chuang, Zhubei (TW)

(72) Inventors: Ming-Hsi Chuang, Zhubei (TW); Chi-An Li, Zhubei (TW); Zer-Ran Yu, Chiayi (TW); Shuen-Ane Kang, Taichung (TW); Chu-Ting Liu, Zhubei (TW); Lin-Hsiang Chuang, Zhubei (TW); Chiu-Ying Peng, Zhubei (TW); I-Lung Yu, Zhubei (TW); Cheng-Yu Chi, Zhubei (TW); Hsin-Yu Chung, Zhubei (TW)

(73) Assignee: Ming-Hsi Chuang, Zhubei (TW)

( * ) Notice: Subject to any disclaimer, the term of this patent is extended or adjusted under 35 U.S.C. 154(b) by 0 days.

(21) Appl. No.: 14/965,965

(22) Filed: Dec. 11, 2015

(30) Foreign Application Priority Data

Sep. 8, 2015 (TW) .............................. 104129687 A

(51) Int. Cl.
*C07C 51/47* (2006.01)
*C07C 39/19* (2006.01)
*B01D 15/26* (2006.01)
*B01D 15/40* (2006.01)

(52) U.S. Cl.
CPC ............ *C07C 51/47* (2013.01); *B01D 15/265* (2013.01); *B01D 15/40* (2013.01)

(58) Field of Classification Search
None
See application file for complete search history.

(56) References Cited

PUBLICATIONS

Lee et al. (Separation and Purification Technology, 2007, 54, p. 130).*

\* cited by examiner

*Primary Examiner* — Sudhakar Katakam
*Assistant Examiner* — Jennifer C Sawyer
(74) *Attorney, Agent, or Firm* — Jackson IPG PLLC; Demian K. Jackson

(57) ABSTRACT

A method of making, separating, and purifying artepillin C in propolis includes mixing propolis with ethanol to obtain a propolis-ethanol extract; providing supercritical carbon dioxide and the propolis-ethanol extract to a chromatographic column to separate wax, artepillin C, and flavonoids; providing supercritical carbon dioxide, the artepillin C, and the flavonoids to an adsorption column to remove the flavonoids; keeping the adsorption column still; and providing ethanol to the adsorption column to obtain the purified artepillin C.

9 Claims, 3 Drawing Sheets

US 9,517,998 B1

DEVICE METHOD OF MAKING, SEPARATING, AND PURIFYING ARTEPILLIN C IN PROPOLIS

BACKGROUND OF THE INVENTION

1. Technical Field

The present invention relates generally to purification of active component of propolis, and more particularly to a method of massively making, separating, and purifying artepillin C in propolis.

2. Description of Related Art

Propolis has been used in traditional medicines for thousands of years. It has various physiological activities, such as anti-cancer activity, antioxidant activity, anti-inflammatory activity, and antibacterial activity. Propolis has many compounds of biological activities, such as cinnamic acid derivative, flavonoid, ester, aromatic aldehyde, ethanol, terpenoid compound, and artepillin C, and flavonoid derivative, aromatic carboxylic acid derivative, and phenols derivative are used in antibacterial and antioxidant treatments.

European Patent, EP0976399B1, teaches a conventional method of extracting and purifying flavonoids and artepillin C from propolis. In this method, an organic solvent is used to remove wax in the propolis. But, the bad result is that flavonoids and artepillin C are damaged by the solvent, and there will be residual problem.

Another European Patent, WO2005094853A1, uses triglyceride or fatty acid as a solvent to remove artepillin C from propolis. Chinese Patent, CN1879656A, uses a surfactant, cyclodextrins for example, to increase water solubility of the functional components of propolis. Another Chinese Patent, CN1108057A, provides water-soluble propolis, which is made by soaking propolis in glycerol, and then heating, stirring, and filtering it. Such water soluble propolis has wax, and the wax greatly reduces the purity of flavonoids and artepillin C.

Chinese Patent, CN101244086B, discloses a method of extracting propolis by supercritical carbon dioxide, wherein a ratio by weight of fine riversands and propolis is 5.3:1, an extracting temperature is 55° C., and a pressure is 30 MPa. Chinese Patent, CN101099547B, provides a method of extracting water-soluble propolis extracts from propolis. These two patents are unable to extract the entire flavonoid and artepillin C from propolis.

In conclusion, the known conventional propolis extracting and purifying methods usually have some drawbacks, including complexity, taking a long time, poor purity, and residual organic solvent problem. Sometime, organic solvent is reacted with functional components that damages the functional components, and the residual organic solvent is another serious problem. They have to be improved.

BRIEF SUMMARY OF THE INVENTION

In view of the above, the primary objective of the present invention is to provide a method of making, separating, and purifying artepillin C in propolis, which may massively produce artepillin C, and maintain biological activity of artepillin C. The method is performed without solvent, therefore there is no residual problem. The method of the present invention has a low cost, and is recyclable, safe, and practicable.

The present invention provides a method of making, separating, and purifying artepilin C in propolis including the following steps:

Extraction, mixing propolis with ethanol to form a mixture, and then removing impurities of the mixture to obtain a propolis-ethanol extract.

Removal of wax, providing supercritical carbon dioxide and the propolis-ethanol extract to a chromatographic column to separate wax, artepillin C, and flavonoids from the propolis-ethanol extract, and then removing the wax at a bottom of the chromatographic column, and collecting the artepillin C and the flavonoids at a top of the chromatographic column;

Separation of the artepillin C and the flavonoids, providing supercritical carbon dioxide, the artepillin C, and the flavonoids to an adsorption column, and then removing the flavonoids at a bottom of the adsorption column, wherein the artepillin C is adsorbed by the adsorption column;

Standing, keeping the adsorption column still for a predetermined time; and

Purification of the artepillin C, providing ethanol to the adsorption column to separate the artepillin C from the adsorption column, and then collecting the artepillin C at a top of the adsorption column.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

The detailed description and technical contents of the present invention will be explained with reference to the accompanying drawings. However, the drawings are for illustration only and cannot be used to limit the present invention.

Figure 1:
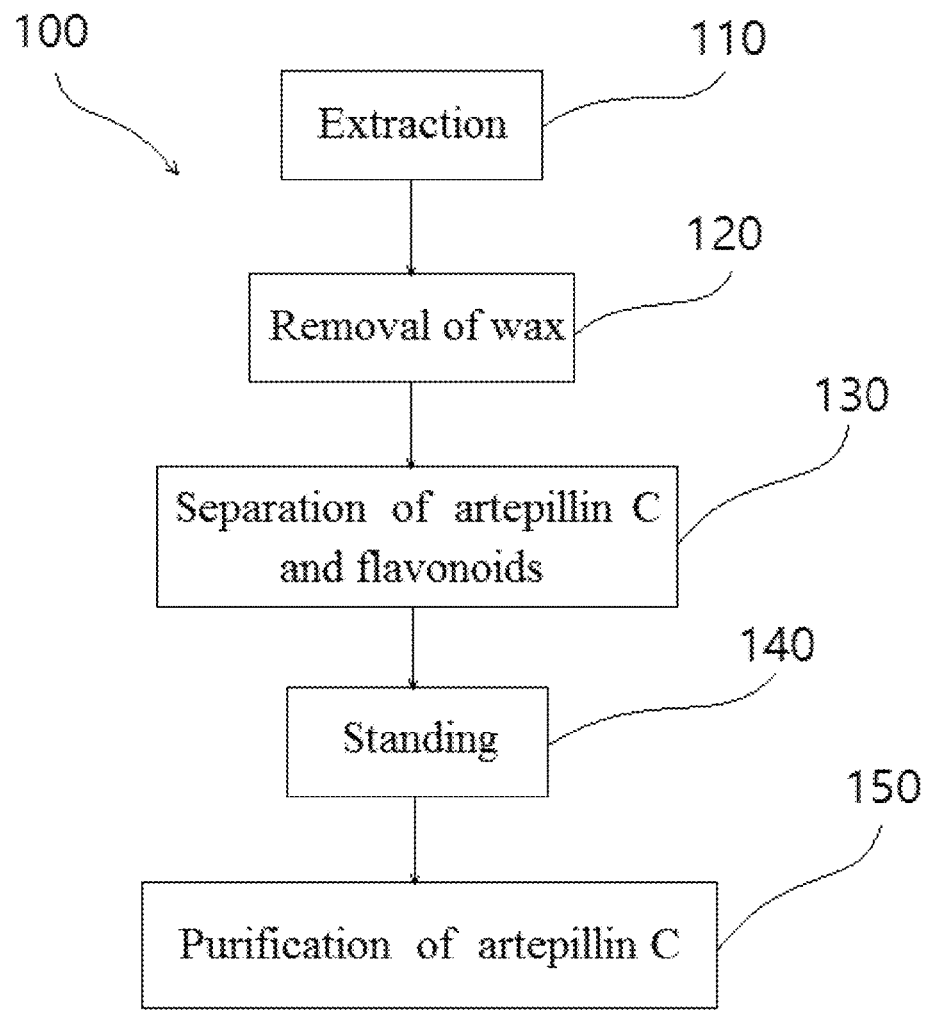
FIG. 1 is a flow chart of a preferred embodiment of the present invention.

As shown in FIG. 1, a method 100 of making, separating, and purifying artepillin C in propolis includes the following steps. The first step is extraction 110, which includes mixing 1-2 kg propolis with ethanol (cosolvent) in a ratio of 1:5-10 (W/V) to obtain a 10-20 L mixture of propolis and ethanol, and then removing impurities from the mixture by centrifugal separation to obtain a propolis-ethanol extract.

The second step is removal of wax 120, which includes providing supercritical carbon dioxide and the propolis-ethanol extract to a chromatographic column to separate artepillin C and flavonoids from the propolis-ethanol extract. Wax in the propolis-ethanol extract is accumulated on a bottom of the chromatographic column for removal, and the separated artepillin C and flavonoids are collected at a top of the chromatographic column. A pressure and a temperature of the chromatographic column is set to 3,000-4,000 psi and 40-60° C., a flow rate of the supercritical carbon dioxide is set to 6-9 L/hr, and a flow rate of the propolis-ethanol extract is set to 1-3 L/hr.

The chromatographic column has a stainless container with 36 mm in an interior diameter and 1,000 mm in a height. A stainless plate is received in the container, which is made of Pro-Pak protruded metal, saddles, rings, structured packing, or knitted packing.

The third step is separation of artepillin C and flavonoids 130. This step is performed under 2,000-3,000 psi and 40-60° C., and a flow rate of the supercritical carbon dioxide is 6-9 L/hr. The supercritical carbon dioxide, artepillin C and flavonoids are sent to an adsorption column for separation. Artepillin C is adsorbed by the adsorption column, and flavonoids are accumulated on a bottom of the adsorption column.

The adsorption column has a stainless container with 36 mm in an interior diameter, 1,000 mm in a height, and the stainless container receives a sorbent, and the sorbent could be silica gel, sephadex, resin, or any material could absorb artepillin C.

The fourth step is standing 140. In this step the adsorption column is kept still for 1-2 hr.

The last step is purification of artepillin C 150. This step is performed under 2,000-3,000 psi and 40-60° C., and a flow rate of ethanol is 1-3 L/hr. Ethanol is provided to the adsorption column to separate the absorbed artepillin C at the bottom of the adsorption column, and then the separated artepillin C is collected at a top of the adsorption column.

The features and advantages of the preferred embodiment of the present invention are compared with the prior arts hereafter.

1. We conduct a test to compare with the extracts (artepillin C, flavonoids, and wax) obtained by three different conventional methods, including extracted by ethanol, extracted by supercritical carbon dioxide, and extracted by supercritical carbon dioxide and cosolvent (ethanol). 1 cc extracts are added to 100 cc water respectively to test color, smell, and taste, we call it sensory evaluation.

Figure 2:
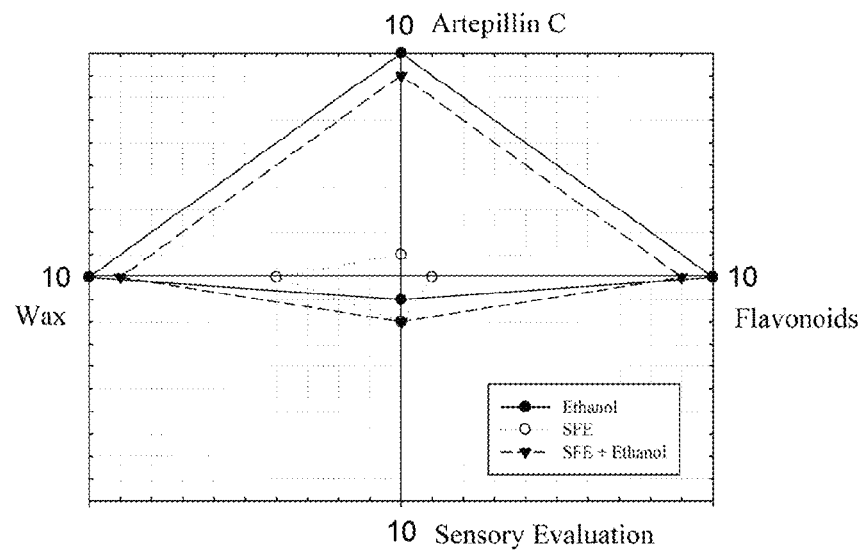
FIG. 2 is a diagram, showing sensory evaluations of wax, artepillin C, and flavonoids extracted by the different conventional methods.

As shown in FIG. 2, the abundance of artepillin C, flavonoids, and wax is scored from 0 to 10 points. 10 points indicate that the abundance of artepillin C, flavonoids, and wax in the extract is the highest level, and 0 indicates that the abundance of artepillin C, flavonoids, and wax in the extract is the lowest level.

The abundance of artepillin C is determined by HPLC quantitative analyzer with a C18 chromatographic column. A concentration of artepillin C is obtained by comparing with the standard curvature of a standard sample and absorbance of a quantitative sample under 320 nm wavelength. The abundance of flavonoids is tested by quercetin as the standard sample and absorbance of a quantitative sample under 415 nm wavelength to obtain a concentration of flavonoids. The abundance of wax is tested by adding 1 cc propolis extract into 100 cc water to collect the suspended matter on the water, and then weighing the dried suspended matter to obtain a concentration of wax. 1 cc extract of propolis is added to 100 cc water to evaluate the sensory evaluation. 0 indicates that color of water is very turbid, sharp flavor, and bad taste, and 10 points indicate that color, smell, and taste of the water are in high acceptable.

As shown in FIG. 2, for the first conventional extracting method, extracted by ethanol (as shown in the curvature of Ethanol), artepillin C, flavonoids, and wax have a great solubility to ethanol, so that it could extract almost every functional components in the propolis. However, while the extracts are added into water or other liquids, the wax of the mixture of hydrocarbon, esters, acids of long-chain nonpolar C24-C34 in propolis will be converted into resin-type crystals in the liquid. Therefore, liquid becomes turbid, and the absorption and usage of the functional components in the propolis will be greatly inhibited. Furthermore, the extract liquid of propolis smells very awful, and wax and fat in the extract liquid will be accumulated in the container.

For the second conventional extracting method, extracted by supercritical carbon dioxide (as shown in the curvature of SFE), it obtains the fat-soluble functional components in propolis only, and no artepillin C and flavonoids is extracted.

For the third conventional extracting method, extracted by supercritical carbon dioxide and the ethanol cosolvent (as shown in the curvature of SFE+Ethanol), an advantage is that the extracting time is short, and a disadvantage is low production. Another disadvantage is that wax and fat in propolis will be extracted at the same time.

For economical issue, the first conventional extracting method is operated in an east way, and has a low cost. For technical issue, the second conventional extracting method is the most effective way to extract artepillin C and flavonoids. The third conventional extracting method obtains almost the same product as the first conventional extracting method, but the cost thereof is about 20 times higher than the first conventional extracting method.

Figure 3:
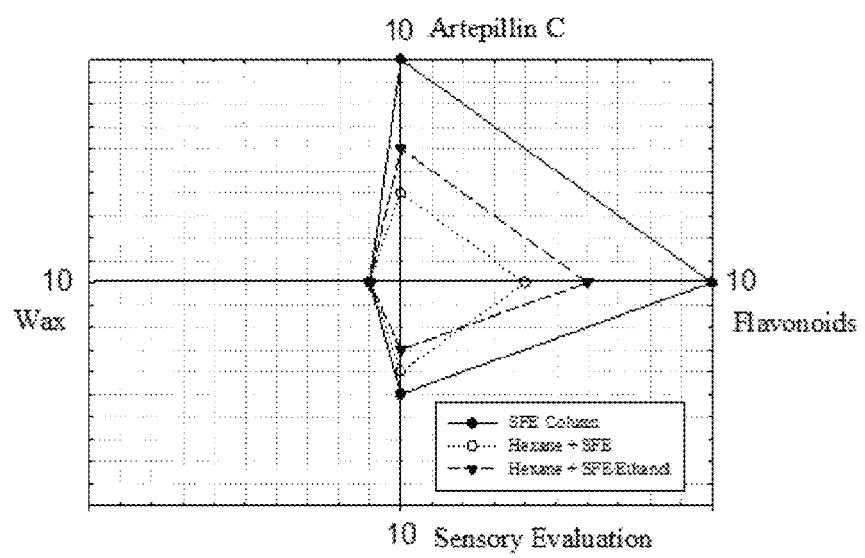
FIG. 3 is a diagram, showing sensory evaluations of wax, artepillin C, and flavonoids extracted by the method of the preferred embodiment of the present invention.

2. FIG. 3 shows the results of the method of the preferred embodiment of the present invention (SFE column). It shows that the method could effectively and totally separate artepillin C and flavonoids from the propolis, and about 95% or more wax in the propolis is removed. The sensory evaluation is better than any of the conventional methods.

Another method, which is shown as the curvature of Hexane+SFE in FIG. 3, is to remove 95% or more wax in the propolis by hexane (organic solvent), and then perform the second conventional extracting method (extracted by supercritical carbon dioxide). It obtains the fat-soluble functional components in propolis only, there still are artepillin C and flavonoids remained in propolis.

Yet another method, which is shown as the curvature of Hexane+SFE/Ethanol in FIG. 3, is to remove 95% or more wax in the propolis by hexane (organic solvent), and then perform the third conventional extracting method (extracted by supercritical carbon dioxide and cosolvent). It obtains about 60% artepillin C and flavonoids only. It is because that hexane makes about 30% artepillin C and flavonoids lost, therefore only about 60% artepillin C and flavonoids is obtained.

The method of the preferred embodiment uses supercritical liquid column chromatographic method to separate wax from propolis, and also totally separate artepillin C and flavonoids at the same time. On the contrary, it will lose about 20-30% artepillin C and flavonoids if hexane is used to remove wax, and furthermore the residual of organic solvent leads some toxic problems.

Figure 4:
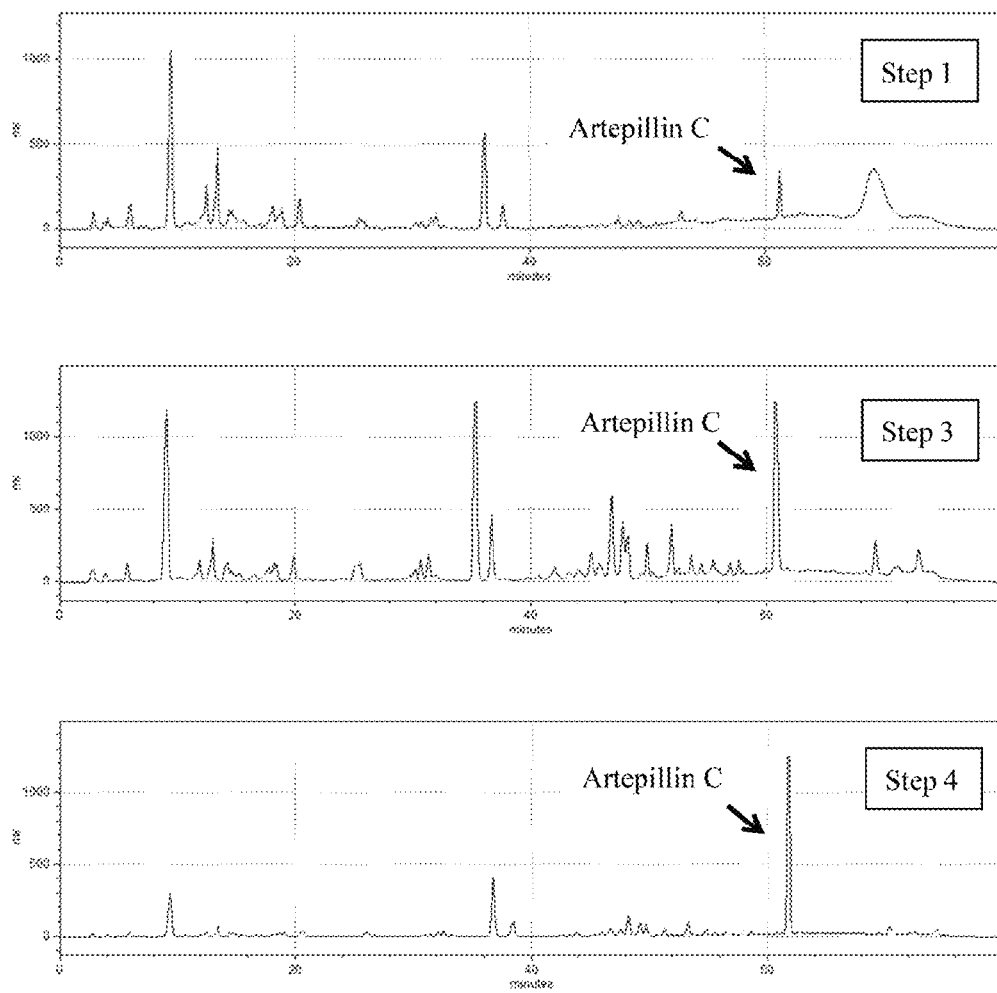
FIG. 4 is a HPLC chromatogram of the preferred embodiment of the present invention.

Besides, as shown in FIG. 4, it shows that a purity of artepillin C obtained by the method of the preferred embodiment of the present invention is up to 90-95%, and it is clearly shown in the HPLC chromatogram of the step 4.

The method of the preferred embodiment may totally extract artepillin C and flavonoids (as shown in Ethanol curvature in FIG. 2) and totally remove wax (as shown in SFE column curvature in FIG. 3) to obtain artepillin C with a purity about 90-95% (as shown in the HPLC chromatogram of the step 4 in FIG. 4).

With the information of FIG. 4 it shows and proofs the following issues:

1. A purity of artepillin C in the propolis-ethanol extract obtained in the step 1 is about 10-15% (as shown in the HPLC chromatogram of the step 1 in FIG. 4).

2. A purity of artepillin C in the propolis separated liquid obtained in the steps 2 and 3 is about 20-25% (as shown in the HPLC chromatogram of the step 3 in FIG. 4).

3. A purity of artepillin C in the propolis purified liquid obtained in the step 5 is about 90-95% (as shown in the HPLC chromatogram of the step 4 in FIG. 4).

In conclusion, the method of the preferred embodiment of the present invention provides supercritical carbon dioxide as solvent, and uses the chromatography and absorption techniques to massively separate and purify artepillin C. It could keep the biological activity of artepillin C. The method of the preferred embodiment of the present invention has a simple procedure, and no residual solvent problem. It further has some advantages, including low cost, recyclable, safety, and practicable.

It must be pointed out that the embodiments described above are only some preferred embodiments of the present invention. All equivalent structures which employ the concepts disclosed in this specification and the appended claims should fall within the scope of the present invention.

What is claimed is:

1. A method of obtaining artepillin C in propolis, comprising the steps of:

mixing propolis with ethanol to form a mixture, and then removing impurities of the mixture to obtain a propolis-ethanol extract;

providing supercritical carbon dioxide and the propolis-ethanol extract to a chromatographic column to separate wax, artepillin C, and flavonoids from the propolis-ethanol extract, and then removing the wax at a bottom of the chromatographic column, and collecting the artepillin C and the flavonoids at a top of the chromatographic column;

providing supercritical carbon dioxide, the artepillin C, and the flavonoids to an adsorption column, and then removing the flavonoids at a bottom of the adsorption column, wherein the artepillin C is adsorbed by the adsorption column;

keeping the adsorption column still for a predetermined time; and providing ethanol to the adsorption column to separate the artepillin C from the adsorption column, and then collecting the artepillin C at a top of the adsorption column.

2. The method of claim 1, wherein a ratio of the propolis and the ethanol in the mixture is 1:5-10 (W/V), and a volume of the mixture is 10-20 L.

3. The method of claim 2, wherein a weight of the propolis for the mixture is in a range between 1 Kg and 2 Kg.

4. The method of claim 1, wherein the chromatographic column is set to 3,000-4,000 psi and 40-60° C., a flow rate of the supercritical carbon dioxide is set to 6-9 L/hr, and a flow rate of the propolis-ethanol extract is set to 1-3 L/hr for providing the supercritical carbon dioxide and the propolis-ethanol extract to the chromatographic column.

5. The method of claim 4, wherein the chromatographic column has a stainless container with 36 mm in an interior diameter and 1,000 mm in a height; a stainless plate is received in the container, and the plate is made of a material selected from the group consisting of Pro-Pak protruded metal, saddles, rings, structured packing, and knitted packing.

6. The method of claim 1, wherein the adsorption column is set to 2,000-3,000 psi and 40-60° C., and a flow rate of the supercritical carbon dioxide is set to 6-9 L/hr for providing the supercritical carbon dioxide to the adsorption column.

7. The method of claim 6, wherein the adsorption column has a stainless container with 36 mm in an interior diameter and 1,000 mm in a height, and the stainless container receives a sorbent, wherein the sorbent is selected from the group consisting of silica gel, sephadex, and resin.

8. The method of claim 1, wherein the adsorption column is kept still for 1-2 hr.

9. The method of claim 1, wherein the adsorption column is set to 2,000-3,000 psi and 40-60° C., and a flow rate of the ethanol is 1-3 L/hr for providing the ethanol to the adsorption column.

* * * * *